United States Patent [19]

Nesburn et al.

[11] Patent Number: 5,294,314

[45] Date of Patent: * Mar. 15, 1994

[54] METHOD OF CROSSLINKING AMINO ACID CONTAINING POLYMERS USING PHOTOACTIVATABLE CHEMICAL CROSSLINKERS

[75] Inventors: Anthony B. Nesburn, Malibu, Calif.; Michael Gorin, Rockville, Md.; Marvin Martinez, Glendale, Calif.; M. Cristina Kenney, Malibu, Calif.; Ezra Maguen, Los Angeles, Calif.

[73] Assignee: Cedars-Sinai Medical Center, Los Angeles, Calif.

[*] Notice: The portion of the term of this patent subsequent to Jun. 18, 2008 has been disclaimed.

[21] Appl. No.: 659,497

[22] Filed: Feb. 22, 1991

Related U.S. Application Data

[63] Continuation of Ser. No. 159,603, Feb. 24, 1988.

[51] Int. Cl.$^5$ .............................................. C07K 3/00
[52] U.S. Cl. .......................... 204/157.68; 204/157.63; 623/6; 128/DIG. 8
[58] Field of Search ...................... 204/157.68, 157.63; 623/6, 7; 128/DIG. 8

[56] References Cited

U.S. PATENT DOCUMENTS

| | | | |
|---|---|---|---|
| 4,505,855 | 3/1985 | Burns et al. | 204/157.68 |
| 4,511,478 | 4/1985 | Nowinski et al. | 210/691 |
| 4,597,999 | 7/1986 | Lingwood | 204/157.68 |
| 4,883,487 | 11/1989 | Yoshizato | 623/901 |
| 5,024,742 | 6/1991 | Nesburn et al. | 204/157.9 |

Primary Examiner—John Niebling
Assistant Examiner—Kishor Mayekar
Attorney, Agent, or Firm—Lyon & Lyon

[57] ABSTRACT

A method for molecularly crosslinking amino acid containing polymers by photoactivating chemical crosslinkers which have been combined with the polymers. Collagen crosslinked by this method can be used as a bioadhesive for sutureless closures of the skin and eye or as a superhydrated material for contact lenses, moist bandage contact lens, lens or corneal implant material, or as a drug delivery mechanism.

3 Claims, No Drawings

METHOD OF CROSSLINKING AMINO ACID CONTAINING POLYMERS USING PHOTOACTIVATABLE CHEMICAL CROSSLINKERS

This is a continuation of co-pending application Ser. No. 07/159,603, filed on Feb. 24, 1988.

FIELD OF THE INVENTION

This invention relates to methods for molecularly crosslinking amino acid containing polymers by photoactivating chemical crosslinking reagents which have been combined with the polymers. More particularly, the invention relates to methods for molecularly crosslinking collagen by photoactivating heterobifunctional crosslinking reagents which have been combined with collagen. Upon photoactivation, reactive groups on these bifunctional reagents crosslink the collagen by forming bridges between amino acid side chains on the collagen molecule.

BACKGROUND OF THE INVENTION

Chemical crosslinkers have been used to study the molecular organization of cell membranes and to understand the way in which various molecules interact with one another at the inner or outer surface of the membrane (Peters, K., Richards, F. M., Ann. Rev. Biochem. 46:523-51, 1977). Protein structural studies utilizing chemical crosslinking began during the 1950's with the work of Zahn (Angew. Chem. 67:561-572, 1955; Makromol. Chem. 18:201-216, 1955; Makromol. Chem. 72:126-152, 1958) and continued in the 1960's, primarily with the work of Wold and his colleagues (J. Biol. Chem. 236:106-111, 1961). In addition, crosslinkers have been used to artificially crosslink and stabilize tissue (Nimni, M., Biorheology, 17:5182 1980).

Crosslinking techniques for the membrane system studies discussed above have made use of bifunctional reagents, which are classified as either homo- or heterobifunctional. Homobifunctional reagents have two identical reactive sites. Heterobifunctional reagents carry two dissimiliar binding sites, one photosensitive and one conventional site. In general, both types of bifunctional reagents act to form chemical crosslinks by introducing bridges between amino acid chains.

The utility of the homobifunctional reagents as crosslinkers in membrane studies has been limited due to several potential inherent problems including random collisional crosslinks, long reaction time, difficulty in controlling reactions and nonselective crosslinking. Random collision-dependent crosslinks can occur at a significant frequency, since molecules nonspecifically crosslink during random collisions in fluid membranes. Such indiscriminate formation of crosslinks can result in a high multiplicity of crosslinked products which are difficult to analyze. It is possible therefore, that low yield crosslinked products would go undetected. These random collisional crosslinks were avoided in some membrane systems with the use of rapidly crosslinking photosensitive agents. (Ji, T. H., Biochimica et Biophysical Acta, 559: 39-69 1979).

In contrast, crosslinking with photosensitive heterobifunctional reagents, can be easily, rapidly and sequentially controlled. Crosslinking with heterobifunctional reagents is accomplished by binding the conventional site on the reagent to one amino group via an amide bound, leaving the second photoactivatable site unbound. Upon photoactivation by the use of ultraviolet or visible irradiation, the photoactivatable site is converted to a species of very high chemical reactivity, which then forms a covalent linkage with another amino acid side chain.

The absorption of ultraviolet or visible radiation by the bifunctional reagent can give rise to two general classes of species produced by cleavage of chemical bonds. Fragmentation can be either at a single bond, resulting in the formation of two free radicals, or at a double bond to carbon or nitrogen. Two types of photosensitive groups are known that result from cleavage at a double bond to carbon or nitrogen: an azide derivative and a diazo derivative. Nitrenes are generated from azides, and carbenes are generated upon photolysis of diazo derivatives. Both nitrenes and carbenes are compounds of very high chemical reactivity.

A common method used for photoactivation of heterobifunctional compounds is irradiation with a short wave ultraviolet lamp, for example, mineral light USV-11. The half time of photolysis with this lamp varies depending on the reagents and is in the order of 10 to 50 seconds. An alternative method, which has several advantages, is flash photolysis for an extremely short period, normally on the order of milli seconds.

Collagen is the single most abundant animal protein. It is the main structural component of mammalian tissues and accounts for about 30% of all mammalian proteins (Nimni, M., Biorheology, 17:51-82, 1980). The molecular structure of collagen consists of three intertwining helical polypeptide chains about 1,050 residues long, wound around each other to form a triple helix.

There is a great amount of uniformity in the amino acid composition of collagen. Glycine forms about 33 percent and proline and hydroxyproline form about 25 percent of the total amount of residues in the polypeptide chains. Proline and hydroxyproline contribute to the rigidity of the molecule in that the beta C is linked to the peptide nitrogen by the side chain, forming a five membered ring thus allowing relatively little freedom of rotation. It is this locking effect by proline and hydroxyproline residues, and the hydrogen bond formation by the hydroxyl group of hydroxyproline, which gives collagen its great stability. The other amino acid residues in the structure include 10 percent alanine and 20 percent polar side chains of arginine, lysine, aspargine and glycine. These do not play a particularly important role in the triple helix but nevertheless are important in the intermolecular linkages which lead to fiber formation.

Crosslinking of the collagen molecules occurs extracellularly and leads to formation of the collagen fiber. This characteristic fiber organization is responsible for the functional integrity of tissues such as bone, cartilage, skin and tendon, and for the structural integrity of blood vessels and most organs.

Both intra- and intermolecular crosslinks in collagens are derived from lysine and hydroxylysine residues. Intramolecular crosslinks are formed when specific lysine and hydroxylysine residues in collagen are oxidatively deaminated to peptide bound aldehydes. Copper, a co-factor with the enzyme lysyl oxidase, causes this modification to take place. The actual formation of the crosslinks takes place via aldol condensation, a spontaneous non-enzymatic reaction where the lysines which are located near the end-terminal region are converted to aldehydes. Intermolecular crosslinks are formed between peptide bound aldehydes and unmodified amino groups of other lysine and hydroxylysine residues. These are the Schiff base type crosslinks, otherwise known as aldamine crosslinks (aldehyde and amino group). This type of crosslink is also considered to be the most physiologically important.

Crosslinking of collagen is a prerequisite for the collagen fibers to withstand the physical stresses to which they are exposed. In past investigations, chemical agents, in particular glutaraldehyde, were found to have application for biosynthesis of intramolecular and intermolecular crosslinks. Artificial crosslinking of collagen with glutaraldehyde has been used commercially to stabilize pig heart valves which are then used in artificial valve replacements (Nimni, M., Biorheology, 17:51-82, 1980). The collagen is crosslinked in this technique with 25 percent glutaraldehyde (commercial) at a neutral pH. The exact glutaraldehyde chemistry of the crosslinking is not clear but Schiff base linkages of glutaraldehyde with two lysine residues are formed.

Many studies have been conducted to develop a substance, either natural or synthetic, which can be employed as a nontraumatic means to help repair tissues after surgery. Major interest in the surgical use of polymeric adhesive materials began in the early sixties (Silverstone et al. Arch. Surg. 81:98, 1962). Initial work was confined to water-soluble systems such as casein and polyvinyl alcohol, but later was expanded to include all available synthetic adhesives and other plastics. Effort at this point was limited to materials with no known local or general toxicity. The 1962 effort of Silverstone and his coworkers was directed more towards wider application of bonding techniques in arterial surgery. In addition to the reinforcement of aneurysms unsuitable for resection, the uses contemplated included reinforcement of junctions after arterial suture or graph, and non-suture anastomosis of small arteries.

Although other materials have been investigated, the most widely used of the tissue adhesives are the cyanoacrylates. These are a homologous series of organic molecules which polymerize and adhere to moist living tissues. Methyl-alpha-cyanoacrylate (MCA) in particular, has been used since 1960 by many investigators as a tissue adhesive for non-suture of bones. MCA is a fluid, monomeric material which under mild pressure, polymerizes in a matter of seconds to produce a thin, strong, adherent film. Although MCA has been shown to be histotoxic, work with higher homologues of the n-alkyl-alpha-cyanoacrylates has indicated that if one proceeds up the homologous series, this histotoxicity decreases.

The toxic effects of synthetic polymers on tissues are related in part to their breakdown products and to the rate at which they are released. All of the polycyanoacrylates degrade in an aqueous medium by the same mechanism—the cleavage of the carbon-to-carbon backbone of the polymer, and the ultimate releasing of formaldehyde and other breakdown products. This mechanism of degradation is essentially the same for all the alkyl cyanoacrylates, though the rate is quite different and depends on the nature of the radical.

It has been reported that the less toxic higher homologues of the cyanoacrylates instantaneously polymerize on tissue substrates and thereby are more effective in inducing homeostasis. Instantaneous polymerization, however, is a disadvantage in surgical applications where it is required to bond two surfaces together, or in adhering cut surfaces of an organ. In these instances, one requires sufficient working time to approximate the surfaces of the tissues before adhesion is permitted to take place.

In order to accommodate these surgical requirements, application techniques of tissue adhesives have been investigated (Matsumoto, T., Tissue Adhesives insurgent, Med Exam. Pub. Co., N.Y. 1972). Tissue adhesives were applied using a spray gun or by a drop method. Polymerization of the adhesive occurred more rapidly when it was applied by spraying. The difference in rates of polymerization was explained by the fact that on spraying, the monomers formed a spreading film, making more surface available to the initiator and thereby a more rapid polymerization rate.

In many surgical techniques the use of the spray method discussed above has a distinct advantage because it is not possible to apply the monomer uniformly and in a thin film with the drop method. Spraying, however, has one disadvantage, in that the monomer polymerizes more rapidly and makes it necessary for the surgeon to work faster. The advantages of and need for an adhesive wherein the surgeon can control the polymerization rate is therefore clear.

In addition, although the reports indicate that cyanoacrylate tissue adhesives offer advantages when used for repair or homeostasis of injured organs, it is known that the presence of the polymer fragment between the incised skin delays wound healing. This is because the polymer fragments prevent the proliferation of fibroblast and microcirculatory vessels bridging the wounded surfaces. Studies conducted comparing the tensile strength of wounds closed by sutures versus cyanoacrylate adhesives, have shown that the glue remains in the tissue for long periods of time, and maximal wound strength is obtained later than for suture closure.

Application of cyanoacrylate adhesives in ophthalmological procedures was introduced in 1963 (Bloomfield, S. et al, Amer. J. Ophthal., 55:742-748, 1963). Since the maintenance of a delicate metabolic and pressure balance within the eye is vital to its optical and electrophysiological function and depends on the integrity of the outer coat, considerable attention in ophthalmology has always been directed towards methods of repair of any process which disrupts the cornea or sclera. Early experience with cyanoacrylate adhesives in the eye was not particularly encouraging. Methyl-2-cyanoacrylates were found to have suitable bond strength, but they proved too toxic.

Over the past century, a number of substances other than the cyanoacrylates have been proposed for sticking one tissue to another, but as with the cyanoacrylates, none appear to have been entirely successful.

Crosslinked gelatins are a leading contender with the cyanoacrylates for the attention and interest of investigators working on tissue bioadhesives. Gelatin is a naturally occurring animal protein with innate adhesive properties. molecular . weights of gelatins range between 30,000 and 120,000 and chemically it is somewhat similar to connective tissue. In 1965, Braunwald and Tatooles (Surgery, 19: 460, 1946) reported the successful use of crosslinked gelatin to control hemorrhage from wounds of the liver and the kidney in dogs. Still later Bonchek and Braunwald (Ann. Surg., 165:420, 1967) also describe the use of crosslinked gelatin to repair incisions in dogs. The main problem with gelatin as a bioadhesive however, is that it is highly susceptible to enzymatic degradation.

Other substances with some adhesive properties have been used to help ocular wounds heal quickly and firmly. Parry and Laszlo reported the use of thrombin for a quick and efficient sealing of conjunctival wounds in corneal scleral incisions in cataract surgery (Brit. J. Opthal., 30:176-178, 1946). Town used fibrin in cataract, glaucoma and traumatic plastic surgery and in keratoplasty (Trans. Amer. Acad. Ophthal. Otolaryng., 54:131-133, 1949). But Young and Favata pointed out that thrombin imparts less tensile strength than ordinary suture materials (War. Med., 6:80-85, 1944).

Another adhesive that has been investigated is fibrin-seal (FS) which is a natural adhesive material composed of fibrinogen, factor VIII, platelet growth factor, antiplasmin thrombin, and calcium chloride. FS has been utilized in vascular surgery to limit blood loss and minimize the amount of vessel trauma and foreign-body reaction by decreasing the number of sutures necessary to achieve a technically satisfactory arterial anastomosis. However, FS causes an increase in the amount of lymphocytic infiltrate in specimens early in the post operative period. As the authors admit, detailed studies to define its role and drawbacks are in order (Ikeossi-O'Connor, M. G., Journal of Surgical Oncology, 23:151-152 1983).

A human fibrin glue has been used in oral surgery (Bull. Group. int. Rech. sc. Stomat. et Odont., 27:171-180, 1984). The substance is made up of two components. One, is highly concentrated fibrinogen and factor VIII together with other plasma proteins, such as albumin and globulin. The second component is a solution of thrombin and calcium chloride, a catalytic agent. The Factor VIII induces the collagen present in the connective tissue to polymerize with the fibrin, forming a bridge between collagen and fibrin. Some known disadvantages of this fibrin glue are that once prepared, it must be used within a short time (so the surgeon must possess accuracy and speed in the operating technique), and the possible transmission of the hepatitis and AIDS viruses.

The foregoing discussion describes the efforts to use a variety of substances of both natural and artificial origin as tissue adhesives. None of these efforts have been completely successful. There still remains both a need for, and a desire for, a tissue adhesive which is simple and practical in application, which is not toxic, which does not retard wound healing, which is readily and harmlessly absorbed and eliminated to normal metabolic pathways once it is served its purpose, and which is without carcinogenic or any other harmful long range potential problems.

The following is a list of desirable criteria for bioadhesives, one or more of which has not been met by the prior materials.
1. Ease of application.
2. Control of polymerization.
3. Flexibility of the resulting bond.
4. Bond strength.
5. Transparency.
6. Low toxicity.
7. Biodegradability

SUMMARY OF THE INVENTION

The practical implementation of the above described techniques has been plagued with many problems. Contrary to prior practice however, we have unexpectedly discovered that the use of photoactivatable crosslinking reagents combined with amino-acid containing polymers produces a highly molecularly crosslinked product upon photoactivation. Collagen crosslinked by this method may then be used as a bioadhesive for sutureless closures of the eye or any other wound in the body, or as a superhydrated material for contact lenses, moist bandage contact lens material, lens or corneal implant material, a wet occlusive bandage, patch graft, implant material to replace silicone in cosmetic plastic surgery, artificial joint lining material or as a drug delivery mechanism which releases medication.

In addition, it is appreciated that this method is equally applicable to binding amino acid containing polymers to other polymers or inorganic materials. Potential clinical applications of this technique would include cementing prosthetic devices securely into place and incorporating collagen centers into contact lenses.

Although the method described in our invention may be used to crosslink any polymer that contains amino acid groups, a preferred use of the method is to crosslink collagen. The following description therefore, is mainly directed to the crosslinking of collagen, but the invention is not intended to be restricted to this use.

In one embodiment of the invention, crosslinked collagen is produced which is useful as a bioadhesive. Tissue adhesives have been used in the past, but they suffer from several problems including toxicity and poor biocompatibility. Our adhesive, on the other hand, is non-toxic and biocompatible since it is made of collagen, the main structural component of mammalian tissues. In addition the material satisfies all the desirable criteria for bioadhesives listed above, including ease of application, ability to control polymerization, flexibility of the resulting bond, high bond strength, transparency, low toxicity and biodegradability.

In this embodiment, processed purified collagen is mixed with photoactivatable heterobifunctional crosslinking reagents. The conventional site on the crosslinker binds to the amino acid groups on the collagen molecules, leaving the other photoactivatable site unbound. This mixture is then applied to the tissue. With appropriate photoactivation, the photoactivated sites on the crosslinking reagents bind to the amino acid groups of collagen in the mixture and the collagen in the cornea, skin and other organs. A sutureless wound closure material is thus produced.

As discussed above, controlling the polymerization rate of previously-known bioadhesives has been difficult. Rapid polymerization creates problems for the surgeon who must work quickly before the adhesive 'sets'. Our adhesive material however, can be applied to the cornea or other parts of the body and once the tissues are in the appropriate position, specific wavelengths of light may be used for final activation, thereby crosslinking, or setting the adhesive.

In another embodiment of the invention, an unexpected superhydrated form of collagen is produced which has application in many areas of medicine. Collagen and other hydrated substances tend to dry out very quickly due to evaporation. This dessication changes the characteristics of the collagen material. In the method of our invention, however, the molecular crosslinks of collagen molecules are an ideal water entrapment matrix, making it possible to have and retain an extremely high water content.

Superhydrated collagen produced by the method of our invention would be an extremely important contact lens material. Soft contact lenses presently dehydrate while on the human eye. They become uncomfortable and change their fit because of this dehydration. Our material used as a soft contact lens would provide an extremely comfortable lens which would not dehydrate.

In addition we propose that as a superhydrated lens implant material with water bound within its interstices, the intraocular lens will not adsorb medication to the extent of the hydrogel intraocular lens currently in use. This property of low adsorption is an important advantage of our material.

Our highly crosslinked collagen is also of great use to plastic surgeons who at present use silicone for implant surgery and inject collagen, which is not highly crosslinked, underneath the skin to eliminate wrinkles. The poorly crosslinked collagen presently used in these techniques must be periodically reinjected because it is subject to breakdown. The highly crosslinked collagen of our invention resists breakdown and is useful as a semipermanent or permanent implant or injection material for plastic surgeons to use in reconstructive and cosmetic surgery.

The superhydrated collagen gel produced by the method of our invention can have incorporated within it a low melting agarose gel containing drug mixture. The collagen may then be placed upon the tissue, where the low melting agarose gel dissolves, thus releasing the bound drug into a specific target area of the body.

DETAILED DESCRIPTION OF THE INVENTION

To date, ten types of collagen have been identified based on their structural differences. Type I collagen is the most abundant in the cornea and has the lowest incidence of antigenicity.

Preferred embodiments of the crosslinking method of the invention use two commercial preparations of this Type I collagen —Vitrogen 100 (or other "Atelocollagen") and Rat Tail Type I. Vitrogen 100 is a purified pepsin-solubilized bovine dermal collagen made by Collagen Corp. In this collagen, the telopeptide responsible for the collagen molecule's antigenicity has been enzymatically cleaved. Rat Tail Type I is a non-pepsin treated collagen made by Collaborative Research, Inc.

The concentration of collagen in the method of the invention varies depending upon the intended use of the crosslinked product. The range may vary from 2.5 mg/ml to 10 mg/ml. These collagen preparation concentrations can be achieved by two well known methods: by dialyzing the collagen against acetate buffer at pH 5, or by lyophilizing known quantities of collagen 15 and then resuspending the collagen in weak acids such as 0.012N HCL or $CH_3COOH$.

The pH of the collagen preparation can exist in a preuse range of pH 2.0 to the buffered preparation as established by Harry S. Geggel et al. ("Collagen Gel for Ocular Surface", Investigative Ophthalmology & Visual Sciences, 1984) at a physiological pH of 7.4.

Crosslinking reagents are then added to the collagen preparation. Crosslinking techniques of our invention make use of heterobifunctional reagents which contain reactive groups that form a bridge between amino acid side chains on the collagen molecule. Bifunctional crosslinkers that may be used in the method of the invention include but are not limited to 4-azidobenzoic acid N-hydroxysuccinimide ester (HSAB) and 6-(4-azido-2-nitrophenyl-amino) hexanoic acid N-hydroxysuccinimide ester (SANAH). These crosslinkers are available from Sigma, Corp.

Unique to the method of the invention, is the fact that while one end of the bifunctional reagents form peptide-like bonds with the collagen amino acid side chains, the other end remains unbound until photoactivation by short-wave ultraviolet light. This end is then converted to a highly reactive compound called a "nitrene" or a "carbene", which in turn bonds with an amino-acid side chain of either molecules of tissue collagen and/or collagen in the preparation.

The concentrations of the crosslinking reagent mixtures used in the invention may vary between 5 Mm and 25 Mm dissolved in a biologically compatible solvent such as DMSO. The concentration of the solvent cannot be less than 50% or the reagents will begin to precipitate. Optimum concentration of the crosslinking reagent is 10 mM established by collagen-reagent (photoactivated) mixture run on Tris-Borate Gels.

Photoactivation of the reagents can be achieved within a wavelength range of 220 nanometers (nm) to 310 nm. The optimum absorbing wavelength is approximately 265 nm with photoactivation time not to exceed 20 minutes. The duration of photoactivation, however, will vary depending on the type of crosslinker used.

The crosslinking efficiency of our reagent is highly dependent on the number of amino-acid side chains it has available. In addition, excess crosslinker may hinder the crosslinking process due to potential competitive binding and internal rearrangement. This means that the active sites of the reagent bound to amino acid side chains via a peptide-like bonding process will be competed for by free reagent. To minimize this occurrence the prephotoactivated mixture of collagen and crosslinking reagent should be run through a Sephadex G-25 column. Fractions can be collected and run through a Spectrophotometer 260-320 nm for determination of peak collagen-reagent fractions. The collected fractions can then be pooled and are ready for photoactivation.

The following examples are intended to illustrate further the practice of the invention and are not intended to limit the scope of the invention in any way.

EXAMPLE I—Procedure for Buffered Collagen Preparation a. Using the method of R. Thoft ("Collagen Gel for Ocular Surface," Investig. Ophth. & Vis. Science) mix cold (40° C.) 0.2M $Na_2HPO_4$ in equal volume with 1.3M NaCl also at the same temperature. Add an equal volume of 0.1M NAOH to the buffer solution.

b. Add eight times (8×) volume of equivalent of Vitrogen to buffer solution.

c. Add cold Phenol red solution (5 mg/100 ml) if pH indicator is needed.

Note: The collagen concentration in the final preparation cannot be less than 1.45 mg/ml.

EXAMPLE II—Procedure for Crosslinking Collagen a. Using the method of H. Geggel and R. Thoft (Investig. Ophth. & Visual Sciences, 1984), pooled fraction of a buffered collagen reagent mixture are poured into either 35 mm sterile culture dishes or polymethyl methacrylate (PMMA) bases lathed to specific curvatures and depth. Precrosslinked gel mixtures are kept at 40° C. until ready for pretreatment and photoactivation.

b. The dishes or bases are then placed in a tissue culture water jacketed incubator at 370° C. with 5% $CO_2$, 95% air for 15 minutes.

c. The dishes or bases are then crosslinked by photoactivation with a short wave UV light (mineral light 254 mm UV lamp Model UVGL-25) for 15-20 minutes.

EXAMPLE III—Procedure for Crosslinking Collagen a. Pooled fractions of buffered collagen reagent from Sephadex columns are poured into 35 mm sterile culture dishes or PMMA bases and kept at 40° C. until ready for use.

b. Using the method of T. Elsdale and T. Bard, J. (Cell Biol., 54:626-637, 1972), dishes or bases are placed in an ammonium hydroxide chamber for between 3 and 30 minutes depending on the degree of rigidity desired.

C. The gels are then photoactivated for 15-20 minutes to achieve crosslinking.

EXAMPLE IV—Washing and Storage of Crosslinked Gels.

a. Gels are removed from culture dishes and PMRA bases and washed twice with distilled H₂O.

b. Gels are placed on a glass plate and a 6 or 8 Mm diameter trephine is used to punch out circular gels which are placed in individual test tubes containing 10 mL of phosphate buffer.

C. Fresh buffer is replaced every 60 minutes for 4 to 6 hours.

d. Gels are stored in Balanced Salt Solution or 0.9% sodium chloride.

Note: Continuous exhaustive washing may occur in PBS, BSS, NaCl (irrigation) or distilled $H_2O$.

We claim:

1. A method of preparing a superhydrated molecularly crosslinked collagen for use as a contact lens material comprising:
   a. combining two or more collagen molecules with a photoactivatable heterobifunctional crosslinking agent having a conventional site and a photoactivatable site such that the conventional site on the crosslinking agent is bound to the collagen molecule, and the other photoactivatable site on the crosslinking agent is unbound, such that upon photoactivation, crosslinks are formed when the photoactivated site on the crosslinking agent binds to another collagen molecule;
   b. photoactivating the collagen-crosslinking agent combination to form said crosslinks; and
   c. incorporating the said two or more collagen molecules into a contact lens.

2. A method of preparing a highly crosslinked collagen for implant surgery comprising:
   a. combining two or more collagen molecules with a photoactivatable heterobifunctional crosslinking agent having a conventional site and a photoactivatable site such that the conventional site on the crosslinking agent is bound to the collagen molecule, and the other photoactivatable site on the crosslinking agent is unbound, such that upon photoactivation, crosslinks are formed when the photoactivated site on the crosslinking agent binds to another collagen molecule;
   b. photoactivating the collagen-crosslinking agent combination to form said crosslinks; and
   c. incorporating the said two or more collagen molecules into a surgical implant.

3. A method of preparing a highly crosslinked collagen for injection material comprising:
   a. combining two or more collagen molecules with a photoactivatable heterobifunctional crosslinking agent having a conventional site and a photoactivatable site such that the conventional site on the crosslinking agent is bound to the collagen molecule, and the other photoactivatable site on the crosslinking agent is unbound, such that upon photoactivation, crosslinks are formed when the photoactivated site on the crosslinking agent binds to another collagen molecule;
   b. photoactivating the collagen-crosslinking agent combination to form said crosslinks; and
   c. incorporating the said two or more collagen molecules into an injection material.

* * * * *